United States Patent [19]
van der Zel

[11] Patent Number: 5,909,612
[45] Date of Patent: Jun. 1, 1999

[54] METHOD FOR MANUFACTURING A DENTAL RESTORATION, IN WHICH A REFRACTORY MODEL IS COATED WITH A POWDERED METAL-CONTAINING COMPOSITION

[75] Inventor: Joseph Maria van der Zel, Hoorn, Netherlands

[73] Assignee: Elephant Edelmetaal B.V., PM Hoorn, Netherlands

[21] Appl. No.: 08/973,992

[22] PCT Filed: Jun. 14, 1996

[86] PCT No.: PCT/NL96/00245

§ 371 Date: May 11, 1998

§ 102(e) Date: May 11, 1998

[87] PCT Pub. No.: WO97/00064

PCT Pub. Date: Jan. 3, 1997

[30] Foreign Application Priority Data

Jun. 15, 1995 [NL] Netherlands .......................... 1000580

[51] Int. Cl.$^6$ ...................................................... B22F 7/00
[52] U.S. Cl. ................................................. 419/5; 419/27
[58] Field of Search ....................................... 419/2, 5, 27

[56] References Cited

U.S. PATENT DOCUMENTS

| | | |
|---|---|---|
| 4,742,861 | 5/1988 | Shoher et al. . |
| 5,143,692 | 9/1992 | Van Der Zel ................................ 419/8 |
| 5,332,622 | 7/1994 | Shoher et al. . |
| 5,336,091 | 8/1994 | Shoher et al. ............................ 433/215 |
| 5,362,438 | 11/1994 | Van Der Zel .............................. 419/28 |
| 5,453,290 | 9/1995 | Van Der Zel ........................... 427/2.27 |

FOREIGN PATENT DOCUMENTS

| | | |
|---|---|---|
| 0 464 951 A1 | 1/1992 | European Pat. Off. . |
| 0 623 335 | 11/1994 | European Pat. Off. . |
| 35 32 331 A1 | 3/1987 | Germany . |

*Primary Examiner*—Ngoclan Mai
*Attorney, Agent, or Firm*—Stevens, Davis, Miller & Mosher, L.L.P.

[57] ABSTRACT

The invention relates to a method for manufacturing a dental restoration, comprising the steps of applying a powdered dental metal comprising composition to a refractory model mass, which powdered dental metal consist of at least three alloys each having a different solidus temperature, the difference between the successive solidus temperatures always ranging between 25 and 100° C., heating the powdered dental material in such a manner that one porous mass is formed, and infiltrating the porous mass with a filler metal alloy in such a manner that the refractory model mass is provided with a homogenous metal coating.

8 Claims, No Drawings

METHOD FOR MANUFACTURING A DENTAL RESTORATION, IN WHICH A REFRACTORY MODEL IS COATED WITH A POWDERED METAL-CONTAINING COMPOSITION

The invention relates to a method for manufacturing a dental restoration, such as a crown or a bridge. In particular, the invention relates to properly fitting, functional metallic restorations manufactured by sintering metal powders on a refractory material. In such methods it is usual that first a chin layer consisting of a mixture of fine metal powder and a glass fraction is applied to the refractory base. Then a composition of a desired metal alloy in powdered form and a thermoplastic binder is applied, e.g. using a heated wax molding instrument. Finally, a number of heating steps is carried out, resulting in a dental restoration at least partially coated with an alloy of the metal powder.

The conventional method commonly used method heretofore for manufacturing dental restorations from metal, which may optionally be coated with plastic or porcelain, comprises casting a dental alloy according to the so-called "lost wax method". In particular, this method, in which an alloy is poured into a refractory die which has the shape of a burned-out wax model, is characterized by the following steps. In the first step, an impression is taken of the preparation in the mouth using a molding mass, usually consisting of silicone material. In the second step, a positive cast in gypsum is made from this impression. The third step comprises molding a wax model on the gypsum model, which wax model is provided in a fourth step with supply ducts of wax and is embedded in a refractory mass. This die of refractory material is heated to a temperature of 600–1000° C. in step 5. Step 6 consists of pouring a liquid metal into the cavity formed. During cooling, the cast suffers thermic shrinkage, which must be compensated for by the refractory mass, by expansion occurring during heating of the die. Finally, the cast workpiece is finished off in step 7 with ceramically bound flints or hard metal cutters, optionally followed by coating the workpiece with plastic or porcelain.

In more recent developments, which will hereinafter be discussed more extensively, process steps 2–7 can advantageously be replaced by the following three steps.

The positive may be cast in refractory material, instead of in gypsum, and the model can then be burned out at a temperature of 1000–1200° C. The refractory material may consist of a mixture of quartz sand with a given granule distribution and magnesium oxide and biammonium phosphate as binders. This powdered refractory material mixture is mixed with collodial silica to form a slurry, which slurry is poured into the impression of the above step 1, where the slurry binds to form a hard mass within 5–10 minutes.

Now a powdered metal is applied to the resulting refractory model in the locations where such is considered necessary for reasons of reinforcement.

Finally, the powder applied is sintered at a temperature of 1000–1300° C. to form a solid metal mass.

To prevent oxidation, the last step is carried out under a vacuum, which can be carried out only in very special oven designed for the purpose, as described in U.S. Pat. No. 4,702,696. The special oven is so expensive that the method described is not economically feasible for many dental laboratories; the high costs make the process unattractive for implementation in laboratories.

U.S. Pat. No. 3,502,466 describes the making of dental crowns using metal powders and in particular precious metal powders. The metal powder used is first mixed with a binder to form a paste or putty. The binder to be used consists of an adhesive, such as ethyl celluose, and a solvent, e.g. propylene glycol. This binder is liquid which renders molding laborious and the chances of residual undesirable porosity in the final product are substantial.

U.S. Pat. No. 4,661,071 describes a procedure using powders or mixtures of powders that are used according to the more recently developed process for manufacturing dental restorations. The process described has a number of disadvantages. Thus, for instance, a costly high-vacuum oven must be used, which is not economically feasible for every laboratory. Further, for mixing the metal powders to be used, propylene glycol is used which yields a paste-like substance. The application of this relatively liquid composition is not easy because any excess cannot be removed by dabbing with absorbent paper. Moreover, it is hard to realize a controlled dense packing of the metal powder, and the chance of undesirable residual porosity in the final product is substantially increased.

German patents 35 32 331 and 38 41 902 basically describe the same process. However, as starting material, mixtures of non-oxidizing powders as well as of oxidizable powders are used. The powders used are sintered in a commercial porcelain oven under a graphite bell jar. An important disadvantage of the use of a graphite bell jar is that it is not always transparent so that the restoration during processing is hidden from view. As a result, it cannot be seen if the restoration makes contact with the graphite. Alloys having a palladium content of at least 35% take up carbon upon contact with graphite at temperatures as used during the heating cycli in oxidizing the restoration and baking the porcelain. A second disadvantage is the burn-out of the outer wall of the graphite bell jar, which is accompanied by crumbling of fine graphite dust. This may contaminate the dental porcelain and the surroundings of the oven. Graphite dust on the restoration may lead to the formation of gas bubbles in the porcelain due to the formation of carbon monoxide gas during baking of the porcelain.

Besides, the graphite bell jar must be so closed that air oxygen can enter rarely, if ever. In the presence of oxygen the alloy material can oxidize, which gives brittle products of low sintering density.

Another disadvantage of the production process according to the above German patents is that the metal powder is mixed with a binder consisting substantially of water. In an aqueous binder the metal powder particles, so to speak, roll over each other, which renders molding difficult. Although the technique of vibrating and dabbing gives a certain degree of densification of the metal powder, it requires special training. Moreover, this will not always lead to a reproducible porosity-free product.

In the above German patent 38 41 902 a bimodal metal powder is applied, using a glycol-like binder. This almost guarantees a product with residual porosity. An important problem occurring with residual porosity is the fact that after sintering this product is brittle and that the product has a low ductility. For ductility, the elongation at break of the material is considered a standard.

German patent 38 11 628 describes a process in which metal tooth replacement products are realized with paste-like metal powders from palladium, gold and silver. These powders are extremely fine and have an average grain size of 0.5–1.5 μm. As a result of the extreme fineness, this powder is only applicable in very thin layers. This renders it impossible to mold occlusions, bridge portions or other solid dental products in one step.

U.S. Pat. No. 4,814,088 teaches the use of an aggregate of two precious metal powders. A component makes up 1–15% by volume of the mixture and consists of a powder of platinum or palladium, which powder has a grain size preferably 5–10 times larger than the grain size of the second powder. This second powder preferably consists of gold. The powder mixture is formed into a paste-like substance using a binder. The binder may be any organic or synthetic resin, such as ethylene or polyethylene glycol. Such binders are liquid, which causes problems when molding and polishing. Moreover, it cannot be guaranteed that a pore-free product remains.

Finally, reference is made to U.S. Pat. No. 4,742,861. This patent describes a method for forming dental restorations using a mixture of two materials. One of these materials is a high fusing precious metal or a high fusing precious metal alloy which is present in excess. Preference is given to an alloy on the basis of gold, platinum, and palladium. In addition, in a minor proportion a precious metal powder or a precious metal alloy powder, preferably gold powder, is present, which has a fusing point substantially below that of the firstmentioned main component. Using a binder on the basis of an organic or synthetic resin, a kind of putty or paste is formed. Thus the powder can be applied to a refractory base with a brush. However, it has been found that applying with a brush gives a hardly reproducible distribution of the powder, with the result that the powder is applied with gaps.

After applying the putty, the whole is heated to above the fusing point of the low fusing powder but below that of the high fusing powder, thus forming a porous sponge-like structure. This structure is effected because the low fusing component only serves for soldering together the high fusing powder particles at the mutual contact points. Subsequently, the porous structure is brought into contact wish a low fusing filler metal, followed by heating the whole so that the filler metal infiltrates into the porous structure and a solid structure is formed.

During sintering of a high fusing and a low fusing component at a temperature between the fusing points of both components, the sintering temperature should be adjusted very accurately because otherwise a fusing together results which then closes at least part of all pores and access paths. No consistently good result can be guaranteed then since a part of the pores cannot later be filled by a filler. Essentially, this known process requires a temperature control within 10° C.

Experiments have shown chat in such a structure in which a high fusing component is enveloped by a low fusing metal phase, the high fusing component dissolves in the whole structure with difficulty. The high fusing component remains apart and forms islets which adversely affects the homogeneity and thus the corrosion resistance of the metal structure. Moreover, the resistant high fusing phase gives rise to microporosities that cannot be filled by the low fusing filler metal, with the result that the final restoration remains relatively brittle. The restorations obtained according to this known method have a very low vickers hardness, usually within the range of 40–70.

The above gaps are not filled with the filler metal but are left as porosity in the dental workpiece. In the mouth such porosity may give rise to the formation of an oxygen potential over the workpiece after which a dissolving reaction can follow. More in detail, the oxygen potential is formed because deep within the pore a lower oxygen tension prevails than at the outside of the restoration where in fact continuous aeration takes place. Thus metal ions can dissolve from the pore and deposit on the outside of the restoration. This may give rise to staining of the dental workpiece.

Both the first heating step and the step of processing the infiltration with filler metal are carried out by the inventors of U.S. Pat. No. 4,742,861 above a bunsen burner or in a normal oven. Thus no use can be made of dental metal alloys which possess a high strength. These would in fact oxidize with the result that the sintering process is hindered. A flux protective against oxidation, as is often also used during flame soldering or soldering in the oven, cannot be applied in this process because the flux will enter the porous structure and disturb the integrity of the structure.

The object of the present invention is to solve the prior art problems. In particular, it is contemplated to provide a method for providing dentals restorations, such as crowns and bridges, by a powder-metallurgical process in which from the powder metal a homogeneous metal structure having a high hardness, vickers hardnesses above 100 and preferably above 140–150, is realized.

It has been found that if a powder metal mixture consisting of not two but at least three components is used, which components have different solidus temperatures, and in which successive solidus temperatures always differ between 25 and 100° C., a porous product is formed after sintering which has a very uniform open structure. This structure can be excellently infiltrated by a filler metal with a relatively low viscosity and contact angle so that a much more reproducible final product is formed which is substantially pore-free, and which is of homogeneous composition. These metal products prove to have vickers hardness values of at least 100 and usually above 145 or 150 to even above 200.

The method for manufacturing a dental restoration therefore comprises according to the invention the steps of applying a powdered dental metal comprising composition to a refractory model mass, which powdered dental metal consists of at least three alloys each having a different solidus temperature, the difference between the successive solidus temperatures always ranging between 25 and 100° C., heating the powdered dental material in such a manner that one porous mass is formed, and infiltrating the porous mass with a filler metal alloy in such a manner that the refractory model mass is provided with a homogeneous metal coating.

For the purpose of the invention, "sintering" is in general the heating of a powdered metal below the fusing point of that metal, such that densification occurs. In the present description and in connection with the present invention, however, this term is used for a somewhat different temperature treatment. In fact, by this term is now meant that the metal powder mixture is heated in such a manner that densification occurs. This may take place at a temperature which is above the solidus temperature of one or two of the three components.

In a preferred embodiment of the method according to the invention at least three alloys are used, the difference between the successive solidus temperatures always ranging between 30 and 70° C., preferably between 40 and 60° C.

While the two-component system described in U.S. Pat. No. 4,742,861 is in fact too sensitive to the sintering temperature used therein, requires heat constant and thus very expensive ovens, the method according to the invention can be carried out with porcelain ovens known from the prior art, in which temperature variations until about 45° C. occur without this having a largely disadvantageous effect on the properties of the ready product.

According to the invention it hss been found that when a powder mixture of at least 3 alloys is used, which alloys have a mutual difference in solidus temperature of from 25 to 100° C., preferably of from 30 to 70° C., and most preferably of from 40 to 60° C., sintering may be occur within the above temperature range, instead of rather at a fixed temperature, if each of the at least three mixture components are at least present in an amount of at least 10% by weight, based on the total amount of metal powder. Therefore, each of the alloys is preferably used in an amount of at least 10% by weight, based on the total weight of the alloys. A final metal structure is then realized which is continuous so that the low fusing, low viscous filler metal to be used can properly reach all the pores and a ready product having a pore-free structure is formed.

For the rest, the amounts of the at least three powder components is less critical, although in general better results are obtained if powder mixture components having higher solidus temperatures are present in a higher weight percentage. Usually, an upper limit of each of the at least three components of 60% by weight will lead to good results. Excellent results are obtained if a three-component system is used having 10–30% by weight of the component having the lowest solidus temperature and 30–70% by weight of the component having the highest solidus temperature.

The method according to the invention can in fact be carried out as described in U.S. Pat. No. 5,143,962, over which the present invention forms a further development and improvement. The different process steps for manufacturing the restoration as described in this publication are also carried out in the present method. Therefore, in the method according to the invention a powdered dental metal comprising composition will be commonly used which, in addition to the powdered metal, has a thermoplastic polymeric material having a fusing point above 50° C., as described in U.S. Pat. No. 5,143,892. As the base to which this composition is applied a fine-grained and porous refractory model mass is used, as described in the above U.S. patent.

The composition consisting of metal powder and the thermoplastic polymeric binder which generally consists of a wax can be applied to the refractory mold mass with a heated waxing knife or another wax molding instrument.

Besides, it is possible to make a film consisting of a metal powder and a relatively hard wax. This film can be cut to size or fitted otherwise so that the film can be placed on the refractory stump. The advantage of this film making method is that a metal layer of uniform thickness remains. In particular an adhesive wax will offer great advantages as binder during application of the film to the model mass.

Besides, it is observed that the binder used according to U.S. Pat. No. 4,742,861 forms bubbles during heating. This contributes to a non-homogeneous final result.

The metal powder-binder combination is heated after application to the refractory base to a temperature at which the binder melts and is absorbed into the refractory model. As a rule, the binder will be so selected that this temperature is in the vicinity of 50–70° C. The liquid binder penetrates into the porous base through the capillary activity of the base. As a result of the binder phase disappearing from the mixture the metal powder is highly densified and an almost perfect close grain packing results which by means of other methods, such as serrating and dabbing, can be obtained at best by taking great pains.

In a preferred embodiment the refractory model is heated after application of the composition containing the powdered metal to a heating device from below, in such a manner that the thermoplastic material filtrates into the refractory model mass and the metal powder remains on the model mass in densified form. This method guarantees that the model mass itself is heated and then causes the binder to melt. When the binder is heated from the outside, there is the possibility that heating does not take place rapidly enough so that binder with metal powder can flow downwards under the action of gravity before the binder is sucked into the model mass.

After densification of the metal powder phase the binder is burned out of the refractory model mass, followed by sintering the coated model mass to form the contemplated porous structure.

The step of heating the powdered dental material in such a manner that one porous metal mass is formed is, when the powder metal alloys contain oxidizable components, preferably carried out under a quartz glass bell jar with a graphite bottom. Such a bell jar is transparent, which enables the process of restoration to be followed with the eyes. The graphite bottom is inlaid in a refractory bowl so as to substantially prevent graphite contaminations in the oven. Because, furthermore, the graphite has practically no contact with the ambient atmosphere, the bottom plate will burn out only slowly. In addition to an economic advantage, this also means that the laboratory environment remains substantially free of graphite pollution. Besides, the glass bell jar must be fitted tightly against the graphite bottom plate to prevent penetration of oxygen from the air. Oxidation of the alloys used actually leads—as already observed above—to brittle products of low sintering density.

The above sintering step is carried out by heating the coated model mass in an oven under a vacuum of, e.g., 100 torr with in general a temperature gradient of 50–150° C. The heating is continued until a temperature which is usually above the solidus temperature of at least the low fusing component. This sintering temperature is then maintained for some time, e.g. 3–15 minutes, during which the desired porous metal structure is formed. The coated refractory model mass is then cooled.

The at least three different powder metal components must be properly soluble in each other so that in the final structure a one-phase structure is formed. Moreover, the different alloys must properly wet each other. In the light of the given information a skilled worker will be able to find suitable alloy mixtures. In particular alloys showing a great overlap in their composition, e.g. overlapping each other in their composition for at least 70% and most preferably at least 80%, comply with these requirements.

In a next step this coated model mass is brought into contact with a low fusing filler metal. The solidus temperature of this filler metal must be lower than the solidus temperature of the porous metal structure to guarantee that through the capillary activity of the porous metal structure this filler metal filtrates into all the pores. The filler metal must be rapidly taken up by the porous structure without it reacting too much with the sintered porous structure during infiltration. Moreover, the filler metal will have to show a relatively small contact angle or dihedral angle with the porous structure. Excellent results are obtained with filler metals that give a contact angle of less than 30° to the porous structure.

The temperature is then increased further than that at which the filler metal infiltrates, which step is preferably also carried out under the quartz glass bell jar. Finally, this results in a solid metal structure which is of homogeneous composition and is substantially free of porosity.

If the composition of the filler metal overlaps the composition of the porous metal mass at least 80%, and preferably at least 90%, it will anyhow be guaranteed that the metal mass is of homogeneous composition. Moreover, according to the invention excellent results are obtained if the filler metal used is a gold-silver alloy. In particular gold-silver alloys having a gold content between 50 and 70% and a silver content between 50 and 30% give excellent results. These alloys have a solidus temperature of about 1050° C. If, furthermore, some zinc is added, the solidus temperature can be further lowered, if required, e.g. to 950–1020° C.

The use of gold as a filler metal, as proposed in the above U.S. Pat. No. 4,742,861, is less preferred. The fusing point of such a filler metal is too high so that the final product remains somewhat porous because fusing together occurs.

The product obtained according to the method of the invention need not be finished.

The most important advantages of the sintering treatment of the powder metal mixture consisting of at least three components are particularly connected with the ease of building up the structure. Other advantages and embodiments of the present invention will be explained in more detail in the following description.

The method according to the invention makes use of a mixture of metal powders which are sintered in a first phase to form a more or less porous structure. Then the porous structure is infiltrated in a second step.

Although U.S. Pat. No. 4,742,861 also teaches an infiltration step, it gives a poorer result because the pores are not quite filled through the reaction occurring between the infiltrating metal and the porous structure first formed.

In the first phase a presintered firm metal structure of regular porosity is formed. This proper distribution of the porosity is obtained by sintering at least three metal alloys having different fusing or solidus temperatures. In this sintering step shrinkage occurs rarely, if ever. The material therefore remains well in place, and the risk of the material getting loose from the refractory stump through sintering shrinkage and therefore causing a poorer fit is practically impossible.

Infiltration with a filler metal is the second essential heating step in the process according to the invention. Infiltration begins with the presintered firm structure obtained from the at least three metal powders. The presintered structure forms a solid skeleton into which liquid material must infiltrate. The liquid material is applied to the oven structure in a thickness and an amount that the pores are correctly filled. The filling of the pores is based on capillary activity. A liquid with a low contact angle is sucked into the open porous structure. The liquid phase can be applied to the surface as a powder and then be heated to above the yield point. After the infiltration the structure is free of porosity.

Infiltration requires a structure of at least 10% porosity. The filler metal must be of low viscosity and must properly wet the solid material of the first sintering step. However, no intermediate transition compositions must be formed between the liquid filler metal phase and the solid substance because they block the infiltration paths. Ideally, there is the least possible mutual solubility between liquid phase and solid substance. Then the liquid phase is soluble in the solid substance, it becomes transient and filtration is hindered or anyhow inhibited by diffusional solidification. Besides, when the solid substance shows a high solubility in the liquid phase, the solid phase will show structural erosion, sagging, and grain growth. Furthermore, to retain firmness during infiltration, it is necessary that during infiltration the dihedral angle be above zero. To avoid swelling and surface erosion caused by the liquid infiltrating the solid substance, a saturated liquid composition is used.

By using a liquid having a very high gold content, as proposed in U.S. Pat. No. 4,742,861, it will be able to dissolve relatively much solid material, which causes clogging of the infiltration paths. Furthermore, during infiltration with practically pure gold, a greater attack on the grain boundaries of the solid substance occurs, which leads to swelling of the structure. According to an above described preferred embodiment it has surprisingly been found that a composition of about 60% gold and 40% silver less aggressively interacts with gold-silver alloys used in the solid substance. In general, a "presaturated" liquid gives much less penetration into the grain boundaries of the solid substance.

The infiltration process in which pores must be formed rapidly occurs, during which dissolution of grains and fragmentation occur simultaneously. The initial infiltration depth h in a porous structure can be described as follows (Semlank, K. A., and Rhines, F. N., "Rates of Infiltration of Metals", Trans. TMS-AIME, 1958, Vol. 212, 325–331):

$$h=(2/\pi) [r.t.\gamma. \cos \theta/2\mu]^{1/2}$$

in which r is the pore diameter, $\gamma$ the liquid-gas surface energy, t the time, $\theta$ the contact angle between liquid and solid substance, and $\mu$ the viscosity.

Furthermore, by means of the method described in Netherlands patent application 9000189, it is possible to use alloys or metals that are hardly castable, if at all. The powder must have a packing density of preferably 75% to permit sufficient capillary flow of a thermoplastic binder through the powder during the further course of the process. Too low a grain packing leads to a less dense product, while a higher grain packing or too fine a grain packing causes too little mobility of the thermoplastic binder.

The metal powder mixture is mixed with 1–15% by weight of high fusing wax. For that purpose, the powder metal is heated in a beaker together with the weighed amount of wax until the wax melts, and the mixture is stirred until the wax is distributed homogeneously throughout the metal. This mixture allows application on the porous fine-grained refractory model, as is now done by a dental technician in molding a wax model on a gypsum model. A preferably electrically heating waxing knife with a temperature of about 150° C. is used for applying and smoothing the metal/wax mixture. After molding, the metal/wax model can be polished until the outer surface is smooth. Modification is possible at all times, should such be necessary upon subsequent checking of the model. In that event, the model is placed in an opened oven chamber preheated to 450° C., or preferably on a heating plate heated to a temperature of 300–600° C. As the temperature of the model rises, the viscosity of the wax becomes sufficiently low, thus permitting capillary flow. Owing to the high porosity and the fine grain size of the subjacent refractory model mass, the wax flows from the metal powder into the refractory mass by capillary attraction. Thus, a capillary attraction between the metal grains is achieved by the migration of the binder in one direction (perpendicular to the refractory surface).

The addition of chemically precipitated gold powder having a grain size of 0.5–15 $\mu$m to the dental metal powder mixture has proved to be effective in the prevention of crack formation in the final product. Because the gold powder is mixed with the coarser alloy powder, separation could occur. However, by mixing the mixture of both powders with a thermoplastic polymer, no separation takes place.

Besides, metal powders used according to the invention are of the type as also used in U.S. Pat. No. 5,143,692.

The invention will now be further described with reference to the following examples. Unless otherwise indicated, percentages are percentages by weight based on the total amount of substance.

EXAMPLE 1

A stump of refractory material, as also used in the example of U.S. Pat. No. 5,143,692, was fabricated according to standard laboratory methods. First of all, a duplicate mold of addition hardening silicone mass was made. This mold was then treated with a conventional surface expanding agent, and the excess was blown off. Subsequently, a model mass mixed with colloidal silica, consisting of quartz, bonded with 15% magnesium oxide and 15% biammonium phosphate was placed in the duplicate mold.

In particular, 20 g refractory model mass was mixed with 4 ml mixing fluid under a vacuum for 30 seconds. The mixed embedding mass was poured into the duplicate mold with vibration. After 30 minutes the model was removed from the mold, preferably by means of compressed air. The resulting refractory stump was then cleaned with a steam jet blower and then laid in boiling water for a few minutes.

At all locations on the model where metal was to be applied later, a thin layer of a bonding agent was applied, consisting of high fusing porcelain and a fine metal powder (palladium). The high fusing porcelain had the following composition: 65% $SiO_2$, 16% $Al_2O_3$, 12% $K_2O$, 6% $Na_2O$, and 1% CaO. After fusing together the components in a platinum crucible at 1600° C. for 4 hours, the porcelain was cast in water. Then it was ground in an attritor grinder to a fineness of less than 1 μm. The palladium powder had a particle size of less than 10 μm. The porcelain was mixed with the metal powder in a volume ratio of 1:1. The mixture was mixed with polyethylene glycol to form a creamy substance and applied to the model in a thin layer. Then the model was predried for 10 minutes under an opened oven chamber preheated to 700° C. and then baked at 1050° C. for 2 minutes.

This bonding layer was applied to just beyond the preparation boundary if a metal ceramics restoration is to be formed; for inlays, onlays, and crowns with a metal-free shoulder the powder is only applied until where the metal powder will later be applied.

Alloy powder mixtures were composed as given in Table 1. These alloy powder mixtures had a grain size of maximally 45 μm and a median grain size of 27 μm and were mixed with a chemically precipitated spherical gold powder of an average grain size of 10 μm.

These powder mixtures were incorporated into 3.5% thermoplastic polymer ACRAWAX B ((Glyco Chemicals, Inc., U.S.A.), which is a reaction product of a stearic acid and monoethanolamine, to form a paste. The fusing point of this wax was between 83 and 86° C., the flash point in air at 235° C., and it formed a gel with kerosene. This paste was applied to a thin layer of wax, provided on the prepared stump, with an electric waxing knife (set at 65° C.).

In another embodiment a film was formed from the powder mixtures and a soft adhesive wax. The resulting film was cut to fitted pieces which were bonded to the stump and smoothened with a spatula.

In both cases the packing density of the metal powders was 75%.

Both types of coated stumps were then further treated in a similar manner and with similar results.

In particular the stump was arranged on a heating plate having a temperature of 385° C. The wax was sucked into the stump, followed by removing the stump from the heating plate. By sucking off the wax, the metal powder obtained a mat appearance, and the molding smoothened at the surface, which phenomenon was observed after about 50 seconds.

Subsequently, the binder was burned out in a burn-out oven at 320° C. for 15 minutes.

Then the stump was placed under the above described quartz glass bell jar and heated in a porcelain oven (100° C./min.) to the sintering temperature given in Table 1, the whole being maintained for 5 minutes. Subsequently, the sintered composition was allowed to cool to room temperature. Then a creamy substance of filler metal was applied in a thickness of 0.2 mm. The filler metal substance consisted of a mixture of 60% gold and 40% silver in glycol. The mixing liquid was burned out in a burn-out oven at 320° C. for 15 minutes.

The coated stump was then placed again under the quartz glass bell jar. The second sintering step of infiltrating the filler metal and baking a uniform structure is carried out at a temperature which is 10° C. above the temperature in Table 1.

TABLE 1

| | Composition in % by weight | | | |
| --- | --- | --- | --- | --- |
| | First phase powder | | | Filler |
| Component | A | B | C | material |
| Proportion in % by weight | 40 | 40 | 20 | 100 |
| Au | 79.5 | 86 | 75 | 59 |
| Pt | 18 | 11.5 | 9 | |
| Pd | — | — | — | |
| Ag | — | — | 14 | 39 |
| In | 2 | 2 | — | |
| Sn | — | — | — | |
| Zn | 0.5 | 0.5 | 2 | 2 |
| Solidus temperature, ° C. | 1100 | 1050 | 1000 | 900 |
| Liquidus temperature, ° C. | 1220 | 1190 | 1100 | 950 |
| Sintering temperature, ° C. | | 1020 | | 1070 |

In the known manner, the following properties of the metal structure were found: bending strength 713 MPa (SD 24); vickers hardness 120–150; thermal expansion coefficient (measured from 20 to 500° C.) 14.4 μm/m/K.

EXAMPLE 2

Example 1 was repeated using components A, B and C given in Table 2 with a solidus temperature of respectively 1150, 1100 and 1050° C. mixed in the ratio of 50, 35 and 15% by weight.

TABLE 2

| | Composition in % by weight | | | |
| --- | --- | --- | --- | --- |
| | First phase powder | | | Filler |
| Component | A | B | C | material |
| Proportion in % by weight | 50 | 435 | 15 | 100 |
| Au | 0.1 | 77 | 75 | 59.5 |
| Pt | — | 10 | — | |
| Pd | 53 | 8 | 10 | |
| Ag | 37 | 2 | 13 | 40 |
| In | 6 | 1.5 | — | |
| Sn | 3.4 | 0.5 | — | |
| Zn | 0.5 | 0.5 | 2 | 0.5 |
| Solidus temperature, ° C. | 1150 | 1100 | 1050 | 980 |
| Liquidus temperature, ° C. | 1250 | 1200 | 1150 | 1030 |
| Sintering temperature, ° C. | | 1050 | | 1070 |

In the known manner, the following properties of the metal structure were found: bending strength 689 MPa (SD 24); vickers hardness 132–156; thermal expansion coefficient (measured from 20 to 500° C.) 14.9 μm/m/K.

I claim:

1. A method for manufacturing a dental restoration, comprising the steps of applying a powdered dental metal comprising composition to a refractory model mass, which powdered dental metal consists of at least three alloys each having a different solidus temperature, the difference between the successive solidus temperatures always ranging between 25 and 100° C., heating the powdered dental material in such a manner that one porous mass is formed, and infiltrating the porous mass with a filler metal alloy in such a manner that the refractory model mass is provided with a homogeneous metal coating.

2. A process according to claim 1, wherein at least three alloys are used, the difference between the successive solidus temperatures always ranging between 30 and 70° C.

3. A process according to claim 1, wherein each of the alloys is used in an amount of at least 10% by weight, based on the total weight of the alloys.

4. A process according to claim 1, wherein the powdered dental metal comprising composition, in addition to the powdered metal, comprises a thermoplastic polymeric material having a fusing point above 50° C.

5. A process according to claim 4, wherein the refractory model is heated after application of the composition containing the powdered metal to a heating device from below, in such a manner that the thermoplastic material filtrates into the refractory model mass and the metal powder remains on the model mass in densified form.

6. A process according to claim 1, wherein the filler metal used is a metal showing a contact angle of less than 30° to the porous metal mass.

7. A process according to claim 1, wherein the filler metal has a composition overlapping the composition of the porous metal mass to at least 80%, and preferably at least 90%.

8. A process according to claim 1, wherein the step of heating the powdered dental material in such a manner that one porous metal mass is formed is carried out under a quartz glass bell jar with a graphite bottom.

* * * * *